United States Patent [19]
Chen

[11] Patent Number: 5,295,973
[45] Date of Patent: Mar. 22, 1994

[54] SAFETY SYRINGE

[76] Inventor: Long-Hsiung Chen, c/o Hung Hsing Patent Service Center, P.O. Box 55-1670, Taipei (10477), Taiwan

[21] Appl. No.: 71,998

[22] Filed: Jun. 7, 1993

[51] Int. Cl.$^5$ ............................................. A61M 5/32
[52] U.S. Cl. .................................... 604/195; 604/110
[58] Field of Search ............... 604/187, 195, 194, 192, 604/196, 197, 110, 272

[56] References Cited

U.S. PATENT DOCUMENTS

| | | | |
|---|---|---|---|
| 5,047,016 | 9/1991 | Dolgn et al. | 604/195 |
| 5,061,249 | 10/1991 | Campbell | 604/195 |
| 5,171,300 | 12/1992 | Blake et al. | 604/195 |
| 5,205,826 | 4/1993 | Chen | 604/195 |
| 5,232,458 | 8/1993 | Chen | 604/195 |

Primary Examiner—John G. Weiss

[57] ABSTRACT

A hollow needle is adapted to be used in a safety syringe which is automatically blocked by a rigid blocking member after finishing an injection and retraction of the used needle into a syringe cylinder, having a bifurcated slot longitudinally notched in a rear portion of a shank and needle head portion of the hollow needle and a plurality of protrusions annularly formed on a circumferential surface of the shank portion of the needle for an easier, smooth and stable embedding of the needle on the rigid blocking member in the syringe, thereby being helpful for a smooth injection and retraction operation of the needle.

1 Claim, 3 Drawing Sheets

SAFETY SYRINGE

BACKGROUND OF THE INVENTION

A conventional safety syringe also invented by the present inventor of this application was patented on Apr. 27, 1993 of U.S. Pat. No. 5,205,826, which includes a hollow needle preliminarily held in a rigid blocking disk embedded in a rear disk socket perpendicularly formed in a flexible plug inserted in a front portion of the syringe for injection use having a needle head portion formed on a rear portion of the needle, and a plunger slidably held in the syringe for boosting a liquid medicine in the syringe to be injected into a patient through the hollow needle having a needle-head socket recessed in the plunger to be engageable with the needle-head socket for pushing the needle head portion of the needle frontwardly to drive the rigid blocking disk frontwardly to engage the blocking disk into a front disk socket which is normally inclinedly formed in the flexible plug and will be operatively perpendicularly biased in the plug when approximately exhausting the liquid in the syringe and finishing the injection, whereby upon a retraction of the plunger and the needle with the needle head portion received in and coupled to the plunger into the syringe to disengage the needle from the rigid disk, the flexible plug will restore the front socket and the rigid disk embedded in the front socket to be inclinedly positioned in the plug, thereby blocking an outward protruding of the needle retracted in the syringe for preventing its injury or infectious contamination to the surroundings.

However, such a conventional safety syringe may have the following drawbacks:

1. When the hollow needle 2 is held in the rigid blocking member 4 embedded in the flexible plug 13 in the syringe cylinder 11, the needle portion 21 with smooth surface may cause an automatic retraction of the needle 2 upon an injection of the needle tip end 211 into a patient's skin and upon an action by a counter force acted by the patient's skin to influence a normal injection operation.

2. The needle shank portion 22 is not bifurcated at its rear end portion to be lacking of elastic property for the hollow needle, thereby influencing or slowing down the coupling of the plunger 31 with the needle head portion 23 of the needle to cause an unsmooth needle injection and retraction operation for recovering a used needle into the syringe.

It is therefore expected to invent a needle which can be resiliently manipulated, held in a syringe for a smooth operation.

SUMMARY OF THE INVENTION

The object of the present invention is to provide a hollow needle adapted to be used in a safety syringe which is automatically blocked by a rigid blocking member after finishing an injection and retraction of the used needle into a syringe cylinder, having a bifurcated slot longitudinally notched in a rear portion of a shank and needle head portion of the hollow needle and a plurality of protrusions annularly formed on a circumferential surface of the shank portion of the needle for an easier, smooth and stable embedding of the needle on the rigid blocking member in the syringe, thereby being helpful for a smooth injection and retraction operation of the needle.

DETAILED DESCRIPTION

Figures 1, 2, 3:
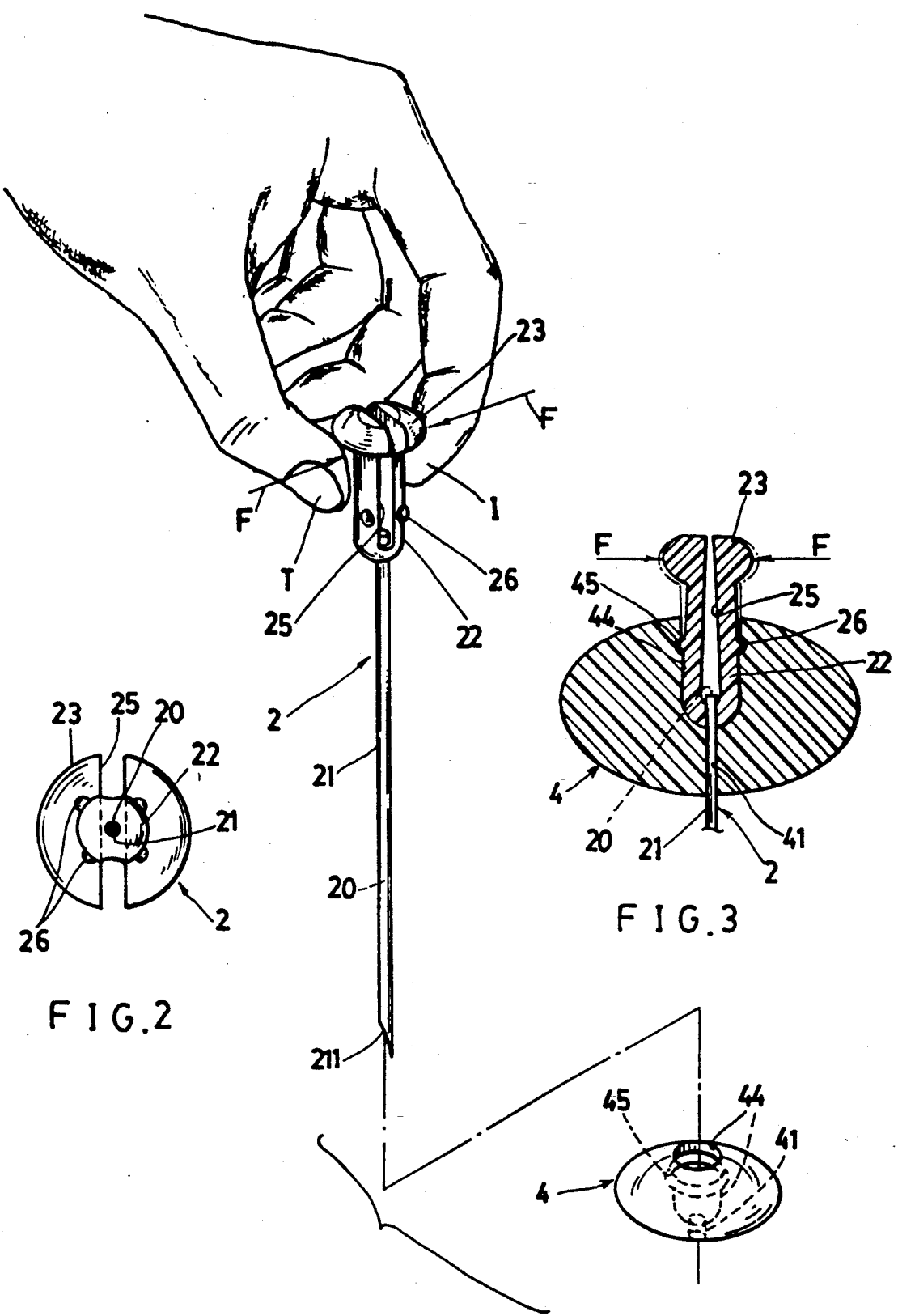
FIG. 1 is a perspective view of the needle and rigid blocking member of the present invention.
FIG. 2 is a front view of the needle when viewed from a tip end of the needle of the present invention.
FIG. 3 is a sectional drawing showing an embedding of the needle in the rigid blocking member in accordance with the present invention.

As shown in the drawing figures, a hollow needle 2 of the present invention is used in a safety syring comprising: a syringe means 1, the hollow needle 2, a plunger means 3, and a rigid blocking member 4 movably held in the syringe means 1. The safety syringe may depend upon the syringe structure and elements of U.S. Pat. No. 5,205,826 invented by the present inventor, except the hollow needle 2 and the rigid blocking member 4 which are modified and explained in detail hereinafter.

Even though this invention merely relates to a resilient needle, the elements of the U.S. Pat. No. 5,205,826 are still used and mentioned herewith for an easy understanding of the use of this invention on the inventors previously issued patent, in which:

The syringe means 1 includes: a syringe cylinder 11 having a hollow bore portion 10 defined in the syringe cylinder 11 and a syringe axis 100 longitudinally existing in a central portion of the syringe cylinder 11 having a plurality of annular extension rings 111 concentrically formed in an inner front portion inside the cylinder 11, a sleeve portion 12 protruded frontwardly from the syringe cylinder 11 having a sleeve hole 121 formed in the sleeve portion 12 for holding a needle portion 21 of the hollow needle 2 in the sleeve hole 121, a flexible plug 13 perferably made of soft, flexible elastomer materials inserted in the front portion inside the cylinder 11 having a central hole 130 for passing the needle portion 21 therethrough, a plurality of annular grooves 132 concentrically formed in the plug 13 engageable with the extension rings 111 in the cylinder 11 for fixing the plug 13 in the cylinder 11, a first disk socket 135 perpendicularly formed in a rear portion of the plug 13 and communicating with a plug guiding port 134 tapered frontwardly from a plug rear surface 133, and a second disk socket 137 normally inclinedly formed in a front portion of the plug 13 communicating with the first disk socket 135 through a throat portion 136 formed between the two disk sockets 135, 137, of which either disk socket 135 or 137 is operatively engageable with the rigid blocking member 4, and a syringe handle 14 formed on a rear end portion of the cylinder 11.

The sockets 135, 137 and the blocking member 4 may be formed as an olive shape, oval shape, a shallow cylindrical shape, or other suitable shapes for a mutual compatible engagement between the blocking member 4 and either socket 135 or 137.

The rigid blocking member 4 is made of rigid plastic or other rigid, hard materials insertable in either socket 135 or 137 in the soft flexible plug 13, and is preferably formed as a circular or cylindrical disk having a longitudinal section of elliptc shape engageable with either disk socket 135 or 137 in the plug 13, having a central through hole 41 formed in a central front portion through the blocking member 4 for passing the needle portion 21 of the hollow needle 2 therethrough, a shank hole 44 formed in a rear portion of the rigid blocking member 4 and communicating with the central through hole 41 formed in the central front portion of the rigid blocking member 4 for engaging a shank portion 22 of the hollow needle 2 into the shank hole 44, and a protrusion groove 45 annularly recessed in a rear portion of the rigid blocking member 4 having a diameter slightly larger than a diameter of the shank hole 44 to engage a plurality of protrusions 26 annularly formed on the needle 2.

Figure 4:
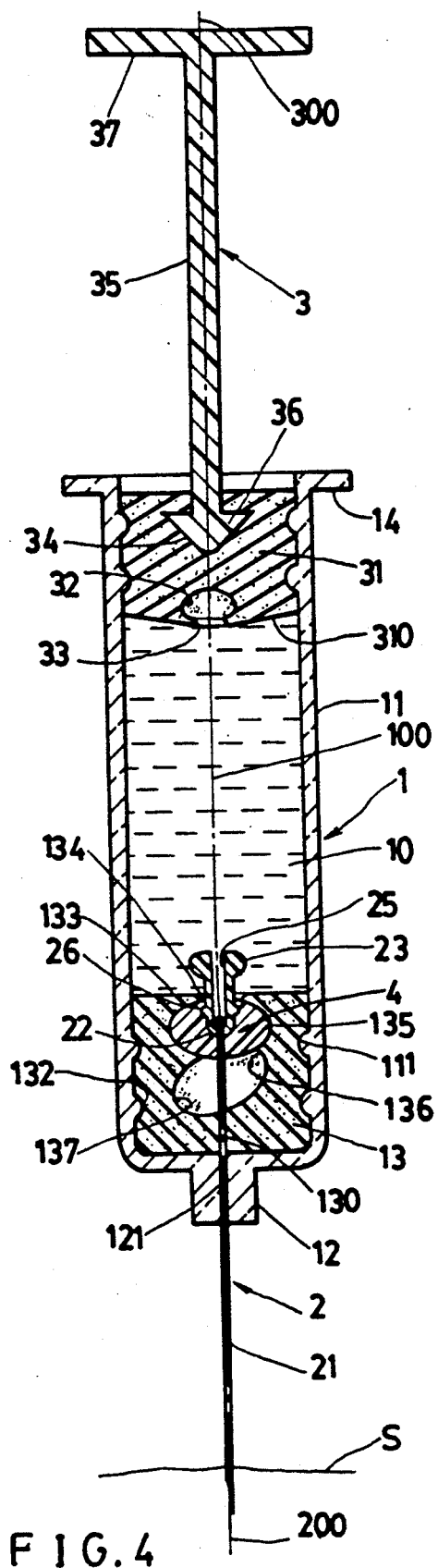
FIG. 4 shows the present invention when performing an injection operation.

The hollow needle 2 includes: a needle portion 21 protruding frontwardly or outwardly through the sleeve hole 121 of the syringe means 1 having a tip end 211 formed on an outer end of the needle and a needle hole 20 formed through the needle portion 21, a shank portion 22 connected with the needle portion 21, a needle head portion 23 formed on a rear portion of the shank portion 22 normally protruding rearwardly beyond a plug rear surface 133 to be engageable with a needle-head socket 32 formed in the plunger means 3, a birufcated slot 25 longitudinally notched in the needle head portion 23 and the shank portion 22 to form a bifurcated needle head portion 23 and shank portion 22 having elastic property of the bifurcated needle head portion and shank portion and communicating with the needle hole 20 formed through the hollow needle 2, a plurality of protrusions 26 annularly formed on a front portion of the shank portion 22, and a needle axis 200 longitudinally existing in a central portion of the needle 2 normally aligned with the syringe axis 100 when held in the plug 13 for normal injection purpose as shown in FIG. 4. The protrusions 26 are engaged with the protrusion groove 45 recessed in the rigid blocking member 4.

The needle head portion 23 of the hollow needle 2 may be formed as elliptic shape to be engaged with an elliptical socket 32 formed in the plunger means 3, but not limited in this invention. The bifurcated slot 25 of the needle will provide the elasticity of the needle and the venting hole the releasing air outwardly during injection.

The plunger means 3 includes: a plunger 31 reciprocatively held in the syringe cylinder 11, the needle head socket 32 recessed in a front end portion of the plunger 31 operatively engageable with the needle head portion 23 having a plunger guiding port 33 tapered rearwardly from a plunger front surface 310 for communicating with the needle-head socket 32 for engageably receiving and coupling the needle head portion 23 when finishing the injection for a retraction of the needle 2 as coupled to the plunger 31 into the syringe cylinder 11, a plunger rod 35 having a coupling member 36 engaged with a rear recess 34 formed in the plunger 31 for coupling the plunger 31 on the rod 35 and a plunger handle 37 for pushing the plunger 31 for boosting liquid medicine in the syringe cylinder 11 for injection use. The needle head socket 32 has a socket center aligned with a plunger axis 300 which is aligned with the syringe axis 100 and longitudinally formed in a center line of the plunger means, and projectively aligned with a needle head center of the needle head portion 23 for a snug engagement of the needle head portion 23 with the needle-head socket 32 of the plunger 31 for coupling the needle 2 to the plunger means 3 which is operatively pushed frontwardly for movably driving the rigid blocking member 4 from a first disk socket 135 to a second disk socket 137 when finishing the injection (FIG. 5) and is then retracted to pull the needle 2 coupled on the plunger 31 to be stored into the syringe cylinder 11, whereby the rigid blocking member 4 will then be automatically restored by the flexible plug 13 to be inclinedly positioned in the plug 13 and the central through hole 41 of the blocking member 4 is then unaligned with the needle axis 200 and syringe axis 100 as shown in FIG. 6 for blocking an outward protrusion of the retracted needle portion 21 for preventing a sting injury or infectious contamination by the needle 2.

Figure 7:
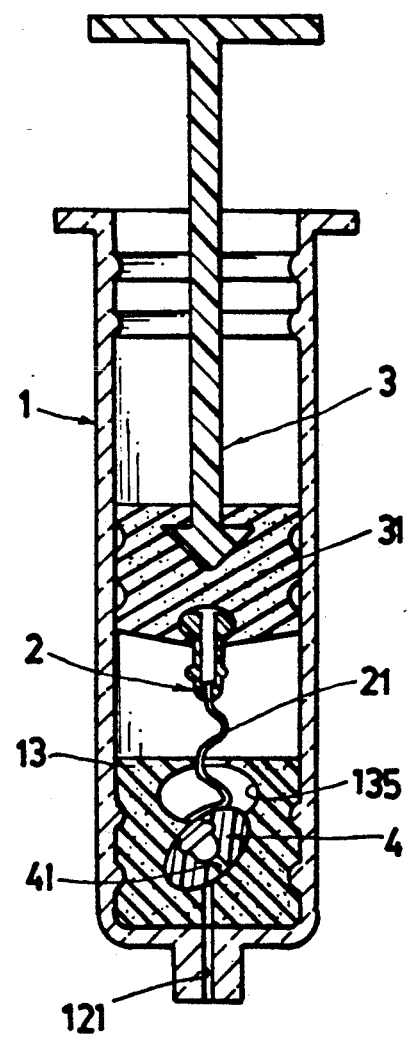

As shown in FIG. 7, a further outward protrusion of the needle 2 will be automatically blocked by the blocking member 4 by bending or deforming the needle tip end 211 which can not be pushed outwardly from the syringe cylinder 11 for a better safety and hygienic protection.

Figure 5:
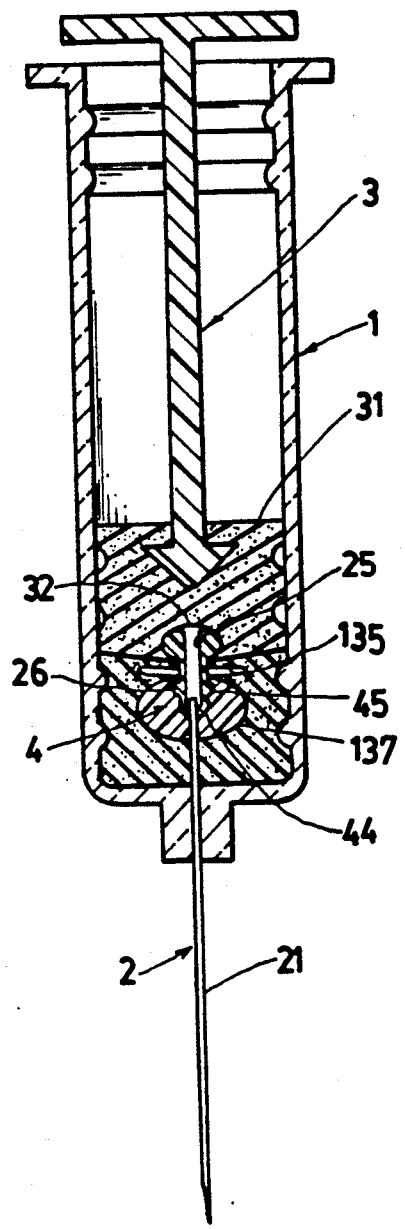
FIG. 5 shows a coupling of the needle with the plunger in accordance with the present invention after finishing an injection operation.
Figure 6:
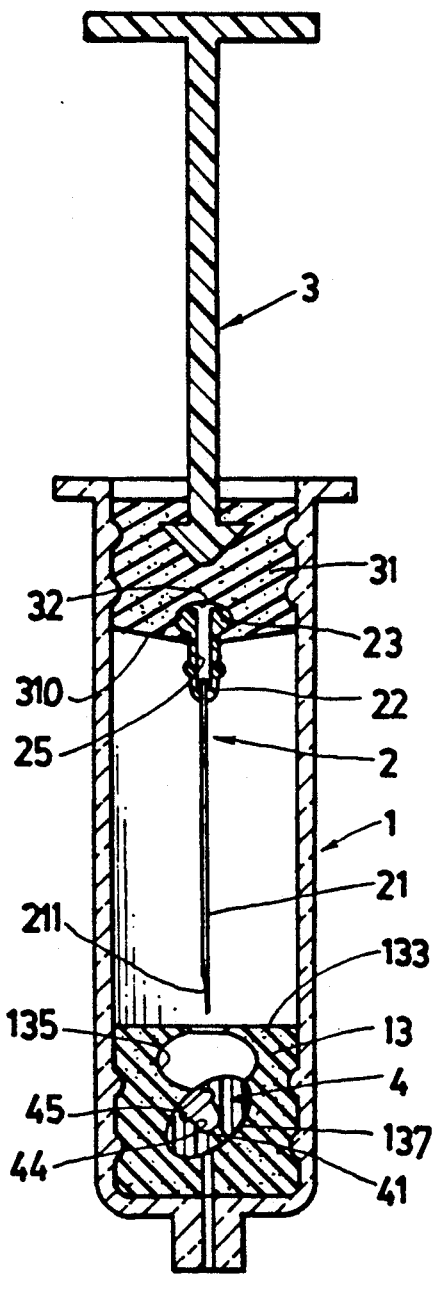
FIG. 6 shows a needle retracted in the syringe of the present invention.

After the retraction of the needle 2 coupled to the plunger 31 into the syringe cylinder 11 as shown in FIG. 6, the flexible plug 13 will be automatically restored by its self elasticity to restore the second socket 137, from its flattened state (blocking member 4 perpendicular to the axis 100) as pressurized by the plunger means 3 as shown in FIG. 5, to be an inclined situation wherein the rigid hard blocking member 4 will be restored to be inclinedly positioned (FIG. 6), thereby blocking the unexpected outwardly protrusion of a retracted needle 2 especially as shown in FIG. 7.

As shown in FIGS. 1–3, the bifurcated needle head portion 23 and shank portion 22 as cut with the bifurcated slot 25 may be compressed or squeezed (F) by a user's thumb T and index finger I, for instance, to easily insert the shank portion 22 into the shank hole 44 of the rigid blocking member 4 to engage the protrusions 26 on the needle 2 with the protrusion groove 45 recessed in the rigid blocking member 4 for a smooth insertion of the needle into the blocking member 4. Then, the bifurcated needle head portion and shank portion will be resiliently restored to be firmly held in the blocking member 4 especially by engaging the protrusions 26 in the groove 45 of the blocking member 4 to prevent an automatic retraction of the needle 2 as backwardly urged by a counter force from a patient's skin S (FIG. 4) when performing an injection.

After coupling the needle head portion 23 of the needle 2 with the socket 32 in the plunger 31, the bifurcated needle head portion which may be formed as an arcuate surface will be easily embedded into the socket 32 due to the elasticity of the bifurcated slot 25. Then, when retracting the finished needle 2 into the syringe cylinder 11, the bifurcated needle head portion 23 will be elastically restored to be firmly engaged with the socket 32 of the plunger 31, ensuring a reliable retraction of the finished needle 2 into the syringe cylinder 11.

By the present invention, a smooth mounting of the needle in the syringe, a smooth injection operation, and a reliable retraction of a used needle into the syringe cylinder will be achieved to be superior to the U.S. Pat. No. 5,205,826 of the inventor's earlier patent.

I claim:
1. A safety syringe comprising:
a syringe cylinder with a front portion and a rear portion,
a flexible plug located inside of said cylinder near the front portion, said plug having front and rear portions, wherein a first disk socket is formed in the rear portion of said plug and a second disk socket, in communication with said first disk socket, is formed forwardly of said first disk socket in the front portion of said plug, said first disk socket of said plug extends perpendicularly outward from the longitudinal axis of said cylinder and said second disk socket of said plug extends outwardly inclined from the longitudinal axis of said cylinder, a rigid blocking member sized to be held in the first or second disk sockets, said member having a central through hole and a larger shank hole extending through a portion of said member, said shank hole having an annular protrusion groove having a diameter larger than the shank hole, a hollow needle having a needle portion and a needle head portion formed on the rear of said needle portion, said needle head portion having a longitudinal bifurcated slot and a plurality of annular protrusions formed on the outer surface of said head portion, said head portion is sized to be received in the shank hole of the blocking member and is retained in the shank hole by said grooves of said hole being engageable with the protrusions of the needle head portion, said head portion also having an enlarged end portion, a plunger held in said syringe cylinder, said plunger having a needle head socket for engageably receiving and coupling with the enlarged end portion of said needle head, in operation said plunger is moved towards the front portion of the syringe cylinder to inject a fluid material held within the cylinder, the plunger then engages said hollow needle that is retained in said rigid blocking member, further forward movement of the plunger causes said needle head socket of the plunger upon the needle head portion and movement of the rigid blocking member from the first disk socket of the plug to the inclined second disk socket of the plug, retraction of the plunger pulls the hollow needle from the rigid blocking member into the syinge cylinder and the rigid blocking member positioned in the inclined second disk socket prevents the needle from aligning with the central through hole of the blocking member to maintain the needle inside of said syringe cylinder.

* * * * *